US012752024B2

(12) United States Patent
Prasad et al.

(10) Patent No.: US 12,752,024 B2
(45) Date of Patent: Oct. 6, 2026

(54) RADIOLABELED STYRYLPYRIDINES AND PHARMACEUTICAL COMPOSITIONS THEREOF

(71) Applicant: Jubilant Draximage, Inc., Kirkland (CA)

(72) Inventors: M Umamaheshwar Prasad, Kirkland (CA); Indranil Nandi, Yardley, PA (US); Vijayaraj Kuniyil Kulangara, Kirkland (CA); Dinesh Kumar Sarwal, Greater Noida (IN); Kamaljeet Pannu, Greater Noida (IN)

(73) Assignee: Jubilant Draximage, Inc. (CA)

(*) Notice: Subject to any disclaimer, the term of this patent is extended or adjusted under 35 U.S.C. 154(b) by 0 days.

(21) Appl. No.: 19/267,544

(22) Filed: Jul. 12, 2025

(65) Prior Publication Data

US 2026/0242337 A1 Aug. 20, 2026

Related U.S. Application Data

(60) Provisional application No. 63/670,611, filed on Jul. 12, 2024.

(51) Int. Cl.
*C07D 213/64* (2006.01)

(52) U.S. Cl.
CPC .................................. *C07D 213/64* (2013.01)

(58) Field of Classification Search
CPC .................................................... C07D 213/64
USPC .......................................................... 546/300
See application file for complete search history.

(56) References Cited

U.S. PATENT DOCUMENTS 7,847,092 B2 * 12/2010 Moon ................... C07B 59/002
536/28.54

* cited by examiner

*Primary Examiner* — Niloofar Rahmani
(74) *Attorney, Agent, or Firm* — William D. Hare; McNeely, Hare & War, LLP

(57) ABSTRACT

The invention discloses radiopharmaceutical composition of Fluorine-18 (F18) labelled styrylpyridine compounds, for use as a medicament for the treatment or diagnosis of a disease or condition associated with build-up of amyloid-β (Aβ) aggregates, preferably F18 Florbetapir, that is free of undesirable nitrosamine drug substance related impurities (NDSRI) and other undesirable nitrosamine impurities. The invention further relates to polymorphic forms of precursors of F18 Florbetapir and their use for preparing F18 Florbetapir.

20 Claims, 2 Drawing Sheets

RADIOLABELED STYRYLPYRIDINES AND PHARMACEUTICAL COMPOSITIONS THEREOF

FIELD OF THE INVENTION

The present invention relates to radiolabelled styrylpyridine, F18 Florbetapir, free of undesirable genotoxic impurities and other undesirable impurities, like nitrosamine drug substance related impurities (NDSRI), and other undesirable nitrosamine impurities.

The present invention further relates to an improved process for the preparation of F18 Florbetapir, free of undesirable genotoxic impurities and other undesirable impurities like nitrosamine drug substance related impurities (NDSRI), and other undesirable nitrosamine impurities.

The present invention further relates to an improved process for the preparation of tosylate precursors of Florbetapir, (AV-105), (E)-2-(2-(2-((5-(4-((tert-butoxycarbonyl)(methyl) amino)styryl)pyridin-2-yl)oxy)ethoxy)ethoxy) ethyl 4-methyl benzenesulfonate, free of undesirable genotoxic impurities like nitrosamine drug substance related impurities (NDSRI), and other undesirable nitrosamine impurities and undesirable polymorphic impurities and their use for the preparation of F18 Florbetapir.

The present invention further relates to polymorphic forms of precursors of F18 Florbetapir, free of undesirable genotoxic impurities and other undesirable impurities, like nitrosamine drug substance related impurities (NDSRI), and other undesirable nitrosamine impurities and undesirable polymorphic impurities and their use for the preparation of F18 Florbetapir.

The present invention further relates to radiopharmaceutical compositions of F18 Florbetapir free of undesirable genotoxic impurities and other undesirable impurities, like undesirable nitrosamine drug substance related impurities (NDSRI) and other undesirable nitrosamine impurities The present invention further relates to the use of radiopharmaceutical compositions of F18 Florbetapir free of undesirable genotoxic impurities and other undesirable impurities, like undesirable nitrosamine drug substance related impurities (NDSRI) and other undesirable nitrosamine impurities as a medicament for the treatment or diagnosis of a disease or condition selected from AD or other disease associated with build-up of amyloid-β (Aβ) aggregates and for selecting patients who are indicated for amyloid beta-directed therapy.

BACKGROUND OF THE INVENTION

Alzheimer's Disease (AD) is a neurodegenerative disorder characterized by the formation of deposits in the brain containing amyloid-β (Aβ) aggregates. The detection of these deposits by histological examination post mortem has been used to confirm a diagnosis of AD.

Positron Emission Tomography (PET) imaging has significantly advanced the diagnosis of AD in living patients, and using PET imaging to examine amyloid load in the brain is an important tool for physicians.

In PET imaging, a positron-emitting radioisotope is introduced into a compound that specifically binds a target molecule, therein the radioisotope then emits signals that are detected in the scanner. F18 is a commonly used radioisotope in PET due to its half-life of about 110 minutes, and because the F18 isotope produces a positron signal that is detected by a PET scanner.

Florbetapir, an F18 radiopharmaceutical developed by Avid, was the first PET imaging agent for AD diagnosis approved by the US Food and Drug Administration (FDA) in 2012. Florbetapir is marketed as Amyvid® by Eli Lilly. Amyvid® is supplied in 10 mL, 30 mL, or 50 ml vials containing 10 mL, 10-30 mL, or 10-50 mL, respectively, of a clear, colorless solution at a strength of 500-1900 MBq/mL F18 Florbetapir at end of synthesis, 4.5 mg sodium ascorbate and 0.1 mL dehydrated alcohol in 0.9% sodium chloride for intravenous injection. The product does not contain any preservative. The pH of the solution is between 5.5 and 7.5. Each vial contains multiple doses and is enclosed in a shielded container to minimize external radiation exposure.

As per the approved FDA label, the recommended dose for Amyvid® is 370 MBq (10 mCi), maximum 50 μg mass dose, administered as a single intravenous bolus in a total volume of 10 mL or less. The F18 in Amyvid® decays by positron (+) emission to 018. A 10-minute PET image is acquired starting 30 to 50 minutes after Amyvid® intravenous injection for diagnosis of AD.

Chemically, Florbetapir, a styrylpyridine, is (E)-4-(2-(6-(2-(2-(2-[F18]-fluoroethoxy) ethoxy)ethoxy)pyridin-3-yl) vinyl)-N-methyl benzenamine, represented by Formula (I):

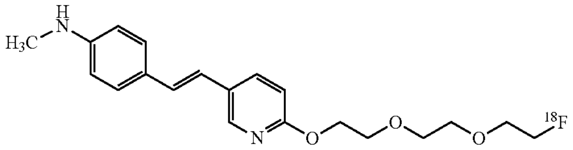 [SMILES: CNc1ccc(/C=C/c2ccc(OCCOCCOCC[18F])nc2)cc1]

Florbetapir manufacturing techniques are disclosed in U.S. Pat. Nos. 7,687,052 and 8,506,929, wherein the process discloses a Wittig reaction between 4-nitro-benzylphosphonate and 6-chloronicotinaldehyde in the presence of sodium methoxide in methanol under refluxing condition that obtained a styrylchloropyridine compound that is used directly for the next step. The alkylation of styrylchloropyridine with 2-(2-(2-fluoroethoxy)ethoxy) ethanol using sodium hydride in tetrahydrofuran (THF) obtained a nitro compound. The nitro compound was reduced using stannous chloride in ethanol to obtain a further intermediate. Monomethylation of the obtained intermediate was achieved using paraformaldehyde, sodium methoxide and sodium borohydride to obtain Florbetapir. The disclosed process suffers from low yield and is deficient of any undesirable impurity control method.

US20100172836 discloses a method of producing the tosylate precursor (E)-2-(2-(2-(5-(4-(tert-butoxycarbonyl (methyl)amino)styryl)pyridin-2-yloxy)ethoxy)ethoxy)ethyl 4-methylbenzenesulfonate ("AV-105"). The method includes the steps of (i) preparing a mono Boc-protected vinylaniline compound; (ii) converting the vinylaniline compound to a methyl, t-butyl carbamate derivative; (iii) reacting 2-halo 5-iodopyridine with triethyleneglycol; (iv) reacting the methyl, t-butyl carbamate derivative of step (ii) with the resultant compound of step (iii) to produce (E)-tert-Butyl 4-(2-(6-(2-(2-(2-hydroxyethoxy)ethoxy)ethoxy) pyridin-3-yl)vinyl) phenyl (methyl) carbamate; and (v) reacting the (E)-tert-Butyl 4-(2-(6-(2-(2-(2-hydroxyethoxy) ethoxy)ethoxy)pyridin-3-yl)vinyl) phenyl (methyl) carbamate with tosyl chloride to form AV-105. The process further discloses producing a radiopharmaceutical composition including a step of reacting the AV-105 tosylate precursor with F18 Fluoride ion in a dimethylsulfoxide (DMSO) solution or other high-boiling point aprotic solvent to produce ((E)-4-(2-(6-(2-i (2-(2-[18F]-fluoroethoxy)ethoxy) ethoxy)pyridin-3-yl)vinyl)-N-methylbenzenamine) (Florbetapir); isolating the Florbetapir and purifying it. The method of producing the radiopharmaceutical composition further includes the step of formulating the F18 Florbetapir in a solution containing about 1.0% to about 15% (v/v) of ethyl alcohol and about 0.1% to about 1.0% (w/v) of an ascorbate salt. However, the process technique disclosed in this patent publication fails to include any methods to control undesirable impurities like nitrosamine impurities.

WO2024107620 discloses polymorphic Form A and polymorphic Form B of the tosylate precursor (AV-105) of Florbetapir, (E)-2-(2-(2-((5-(4-((tert-butoxycarbonyl) (methyl) amino)styryl)pyridin-2-yl)oxy)ethoxy)ethoxy) ethyl 4-methylbenzenesulfonate.

There is an unmet need in the art for: a) robust and safe manufacturing of the F18 labelled tracers free of undesirable nitrosamine impurities, and b) processes that provide a high yield of the overall synthesis to allow the production of quantities of the diagnostic to supply the radiotracer, despite the half-life of 110 min, to facilities without cyclotron or radiopharmaceutical production facility.

The processes disclosed in the published literature fail to provide the control of undesirable genotoxic nitrosamine impurities in F18 Florbetapir. Consequently, there is a need for an improved process for the preparation of F18 Florbetapir that is simple, environmentally friendly, economically viable and industrially feasible for the preparation of F18 Florbetapir, its precursors and radiopharmaceutical compositions of F18 Florbetapir with essential control on nitrosamine impurity levels and undesirable polymorphs.

OBJECT AND SUMMARY OF THE INVENTION

The principal object of the present invention is to overcome or alleviate at least one of the deficiencies of the prior art and provide a useful alternative for providing F18 Florbetapir.

It is an object of the present invention to provide F18 Florbetapir comprising undesirable nitrosamine impurities at levels less than 100 ppm, preferably less than 50 ppm and more preferably less than 20 ppm and other impurities less than 10 μg/ml, preferably less than 5 μg/ml, more preferably less than 3 ug/ml.

It is another object of the present invention to provide a simple, economic and efficient process for the preparation of F18 Florbetapir free of nitrosamine impurities, wherein nitrosamine is selected from the group comprising of nitrosamine drug substance related impurities (NDSRI), specifically N-Nitroso Florbetapir (Formula II), and other nitrosamine impurities selected from ((E)-2-(2-(2-((5-(4-(methyl (nitroso)amino)styryl)pyridin-2-yl)oxy)ethoxy)ethoxy)ethyl 4-methylbenzenesulfonate (Formula XI), (E)-N-(4-(2-(6-(2-(2-(2-hydroxyethoxy)ethoxy)ethoxy)pyridin-3-yl)vinyl) phenyl)-N-methylnitrous amide (Formula VIII), and [N-methyl-N-(4-vinylphenyl)nitrous amide] (Formula V), N-Nitroso mesylate compound of Formula XIII, Nitrosodimethylamine, N-Nitrosodiethylamine, N-Nitrosodiisopropylamine (NDIPA/DIPNA), N-Nitrosoethylisopropylamine (EIPNA), N-Nitrosomethylethylamine (NMEA), N-Nitrosodipropylamine (NPDA), N-Nitrosodibutylamine (NBDA), N-Nitrosomethyldodecylamine, N-Nitroso-N-methyl-N-tetradecylamine, wherein the nitrosamine impurities are less than 100 ppm, preferably less than 50 ppm and more preferably less than 20 ppm and other impurities less than 10 μg/ml, preferably less than 5 μg/ml, more preferably less than 3 ug/ml.

It is another object of the present invention to provide a simple, economic and efficient process for the preparation of tosylate precursor for F18 Florbetapir, AV-105, free of undesirable nitrosamine impurities, wherein nitrosamine is selected from the group comprising of N-Nitroso AV-105, ((E)-2-(2-(2-((5-(4-(methyl(nitroso)amino)styryl) pyridin-2-yl)oxy)ethoxy)ethoxy)ethyl 4-methylbenzenesulfonate (Formula XI), (E)-N-(4-(2-(6-(2-(2-(2-hydroxyethoxy) ethoxy)ethoxy)pyridin-3-yl)vinyl)phenyl)-N-methylnitrous amide (Formula VIII), and [N-methyl-N-(4-vinylphenyl) nitrous amide] (Formula V), Nitrosodimethylamine, N-Nitrosodiethylamine, N-Nitrosodiisopropylamine (NDIPA/DIPNA), N-Nitrosoethylisopropylamine (EIPNA), N-Nitrosomethylethylamine (NMEA), N-Nitrosodipropylamine (NPDA), N-Nitrosodibutylamine (NBDA), N-Nitrosomethyldodecylamine, N-Nitroso-N-methyl-N-tetradecylamine wherein the nitrosamine impurities are less than 100 ppm, preferably less than 50 ppm and more preferably less than 20 ppm.

It is yet another object of the present invention to provide a process for the preparation of tosylate precursor for F18 Florbetapir, AV-105, free of undesirable polymorphic form of AV-105 and undesirable nitrosamine impurities, wherein the undesirable nitrosamine impurities are less than 100 ppm, preferably less than 50 ppm and more preferably less than 20 ppm.

It is yet another object of the present invention to provide polymorphic forms of precursors of F18 Florbetapir, free of genotoxic undesirable nitrosamine impurities and their use for the preparation of F18 Florbetapir, wherein the undesirable nitrosamine impurities are less than 100 ppm, preferably less than 50 ppm and more preferably less than 20 ppm and other impurities less than 10 μg/ml, preferably less than 5 μg/ml, more preferably less than 3 μg/ml.

It is an object of the present invention to provide a radiopharmaceutical composition of F18 Florbetapir having at least one or more pharmaceutically acceptable excipients, wherein the composition comprises undesirable nitrosamine impurities less than 100 ppm, preferably less than 50 ppm and more preferably less than 20 ppm and other impurities less than 10 μg/ml, preferably less than 5 μg/ml, more preferably less than 3 ug/ml.

It is yet another object of the present invention to use radiopharmaceutical composition of F18 Florbetapir, having at least one or more pharmaceutically acceptable excipients, wherein the composition comprises undesirable nitrosamine impurities less than 100 ppm, preferably less than 50 ppm and more preferably less than 20 ppm and other impurities less than 10 μg/ml, preferably less than 5 μg/ml, more preferably less than 3 ug/ml, as a medicament for the treatment or diagnosis of a disease or condition selected from AD or other disease associated with build-up of amyloid-β (Aβ) aggregates and for selecting patients who are indicated for amyloid beta-directed therapy.

DESCRIPTION OF THE INVENTION

Figure 1:
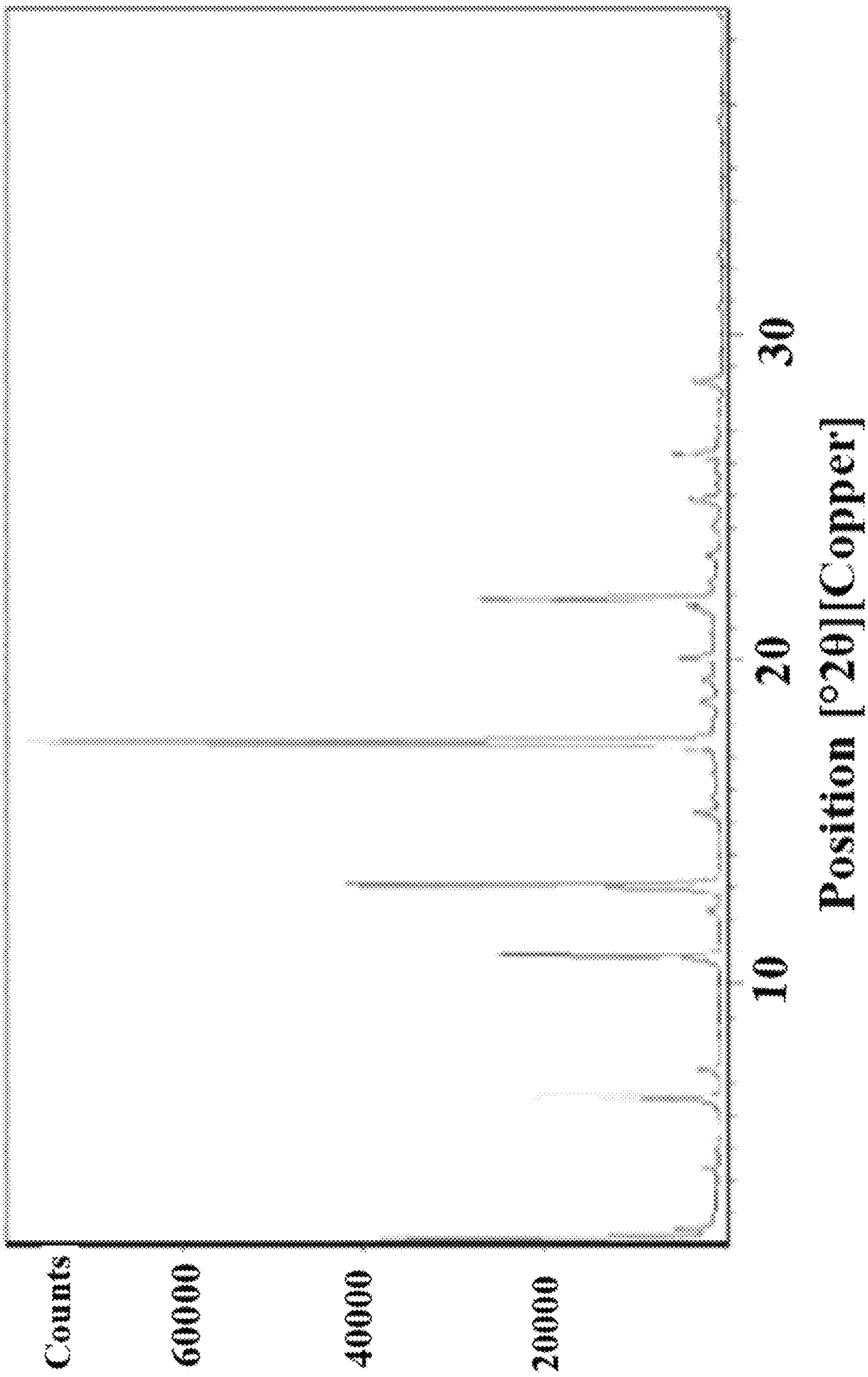
FIG. 1: gives the X-ray powder diffractogram crystalline form mesylate precursor of Formula XII.

While this specification concludes with claims particularly pointing out and distinctly claiming that which is regarded as the invention, it is anticipated that the invention can be more readily understood through reading the following detailed description of the invention and study of the included examples.

The term "about" as used herein in the invention refers to a measurable value such as a parameter, an amount, a temporal duration, and the like, and is meant to encompass variations of and from the specified value, in particular variations of ±10% or less, preferably ±5% or less from the specified value, such variations are appropriate to perform in the disclosed invention. It is to be understood that the value to which the modifier "about" refers is itself also specifically, and preferably, disclosed.

As used in the specification of the present invention, the singular forms "a", "an", and "the" include plural references unless the context clearly dictates otherwise. Thus, for example, a reference to "a process" or "a composition" includes one or more process or composition, with one or more steps or ingredients or elements of the type described herein and/or which will become apparent to those persons skilled in the art upon reading this disclosure and so forth.

As used herein the term "radiochemical purity" refers to the proportion of the total radioactivity in the sample which is present as the desired radiolabelled species. Radiochemical purity is important since it is the radiochemical form, which determines the biodistribution of the radiopharmaceutical. The present invention includes the pharmaceutical composition, wherein the composition has a radiochemical purity of at least 80 percent, preferably 95 percent, most preferably 100 percent for 3 hours at room temperature. Radiochemical purity (RCP) is determined using radio TLC or HPLC and can be defined as the ratio of the (radiolabelled) drug substance peak to the total (radio-labelled) peaks in the chromatogram.

As used herein the terms 'stabilizers' or 'antioxidants' or 'radioprotectants' are used as synonymous words, which refers to an agent which protects organic molecules against radiolytic degradation. These substances or agents prevent oxygen from reacting with other compounds that are susceptible to oxidation. The stabilizer may be able to scavenge radicals, which may be generated, for example, when the radionuclide emits a gamma ray and the gamma ray cleaves a bond between the atoms of organic molecules, thereby forming radicals. Hence, the stabilizer can avoid or reduce that radicals undergo other chemical reactions, which might lead to undesirable, potentially ineffective or even toxic molecules.

As used herein the term 'free radical scavenger' refers to compounds used because in a radiopharmaceutical composition radiolysis is caused by the formation of free radicals such as hydroxyl and superoxide radicals (Garrison, W. M. Chem. Rev. 1987, 87, 381-398). Free radicals are very reactive towards organic molecules. The reactivity of these free radical towards organic molecules can affect the solution stability of a radiopharmaceutical composition. Stabilization of the radiopharmaceutical composition is a recurrent challenge in the development of target-specific radiopharmaceuticals, and radical scavengers are often employed as a stabilizer to minimize radiolysis of the radiolabeled molecules. Some stabilizers are "radical scavenging antioxidants" that readily react with hydroxyl and superoxide radicals.

As used herein the term 'co-solvent' refers to a secondary solvent added to a primary solvent in small amounts to increase the solubility of a poorly-soluble compound in the primary solvent. Co-solvent should be miscible in all proportions to the primary solvent.

Nitrosamines are potent carcinogens in animals and probable carcinogens in humans. Nitrosamines and their precursors can be potentially found out throughout a manufacturing process such as in contaminated raw material/intermediates used in the manufacturing process; use of recovered solvents and recovered catalysts which are not subjected to adequate removal of amine contaminants. Importantly, the most probable reason for their presence during a manufacturing process is the interaction of secondary amines/tertiary amines with nitrite in acidic conditions. ICH M7 (The International Council for Harmonization of Technical Requirements for Pharmaceuticals for Human Use) recommends that these mutagenic carcinogens should be essentially controlled below the acceptable cancer risk level by selecting a manufacturing process that includes essential controls in minimizing or/and complete removal of undesirable nitrosamine impurities to ensure safety of prepared F18 Florbetapir for human use.

Florbetapir, having the chemical structure of Formula I wherein the structure contains a secondary amine, is prone to the formation of undesirable nitrosamine impurities and specifically N-Nitroso Florbetapir of Formula II, which is exclusive for Florbetapir. The published literature does not provide any effective technique to control the formation of known undesirable nitrosamine impurities and N-Nitroso Florbetapir during preparation of Florbetapir, its intermediates, tosylate precursor of F18 Florbetapir, AV-105 and other precursors of F18 Florbetapir. Thus, there is an unmet need in the art for the development of an advantageous process for the preparation of Florbetapir providing Florbetapir free of undesirable nitrosamine impurities. Such a process is provided herein in the present invention.

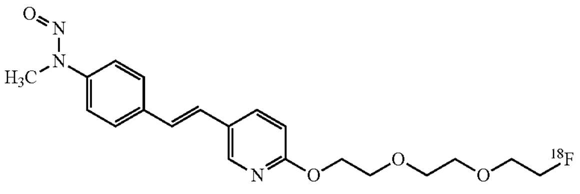 [SMILES: CN(N=O)c1ccc(/C=C/c2ccc(OCCOCCOCC[18F])nc2)cc1]

The present invention relates to F18 Florbetapir of Formula I,

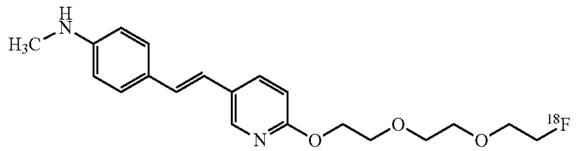 [SMILES: CNc1ccc(/C=C/c2ccc(OCCOCCOCC[18F])nc2)cc1]

has undesirable nitrosamine impurities less than 100 ppm, preferably less than 50 ppm and more preferably less than 20 ppm and other impurities less than 10 µg/ml, preferably less than 5 µg/ml, more preferably less than 3 ug/ml.

The present invention relates to a process for preparing F18 Florbetapir of Formula I,

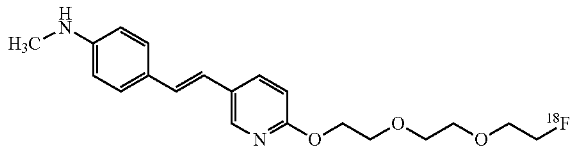 [SMILES: CNc1ccc(/C=C/c2ccc(OCCOCCOCC[18F])nc2)cc1]

comprising the steps of:

(a) methylation of the compound of Formula III with a suitable methylating agent to obtain the compound of Formula IV and with the compound of Formula V being present at less than 10 ppm;

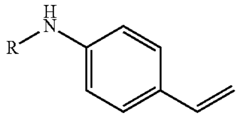

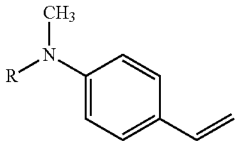

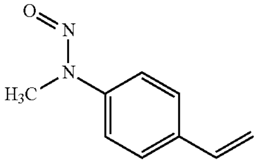

(R) is a N-protecting group (b) reacting the compounds of Formula IV and Formula VI in a suitable solvent in the absence of an organic base using about 2.0 to 3.0 mole equivalents of inorganic base, about 1.5 to 2.0 mole equivalents of phase transfer catalyst to obtain the compound of Formula VII wherein the compound of Formula VIII is present at less than 10 ppm;

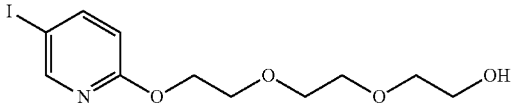

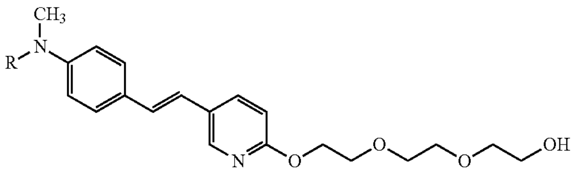

-continued

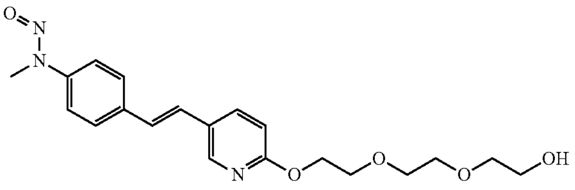

(c) introducing a leaving group into the compound of Formula VII to obtain a compound of Formula IX free of the N-nitroso derivative of Formula IX;

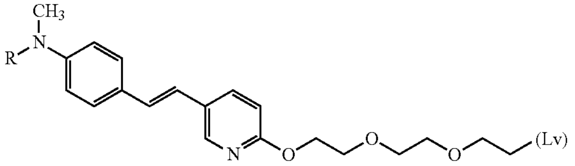

wherein (R) is a N-protecting group and [Lv] is a leaving group; and (d) radiolabeling a compound of Formula IX with a F-18 fluorinating agent and removing the N-protecting agent to obtain a compound of Formula I wherein the F18 Florbetapir obtained has nitrosamine impurities less than 100 ppm, preferably less than 50 ppm and more preferably less than 20 ppm and other impurities less than 10 μg/ml, preferably less than 5 μg/ml, more preferably less than 3 μg/ml.

According to an embodiment of the present invention, the invention relates to a process for preparing AV-105 tosylate precursor of F18 Florbetapir of Formula X, free of undesirable nitrosamine impurities.

According to present invention, the AV-105 tosylate, precursor of F18 Florbetapir, of Formula X is free of undesirable nitrosamine impurities, wherein the undesirable nitrosamine impurity is the N-Nitroso compound of Formula XI.

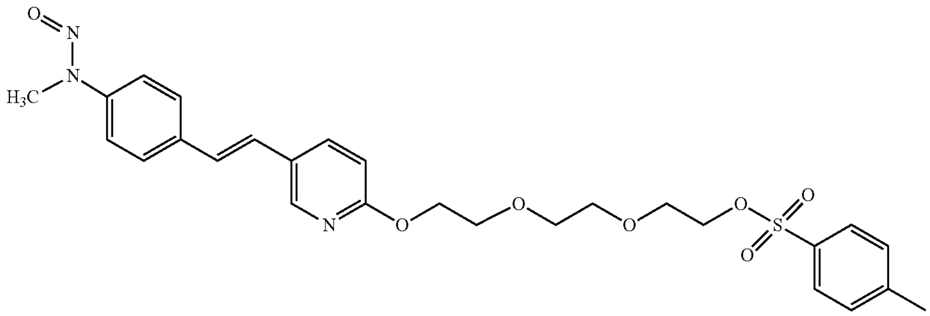

The present invention relates to a process for preparing the AV-105 tosylate precursor of Fluorine 18 Florbetapir of Formula X,

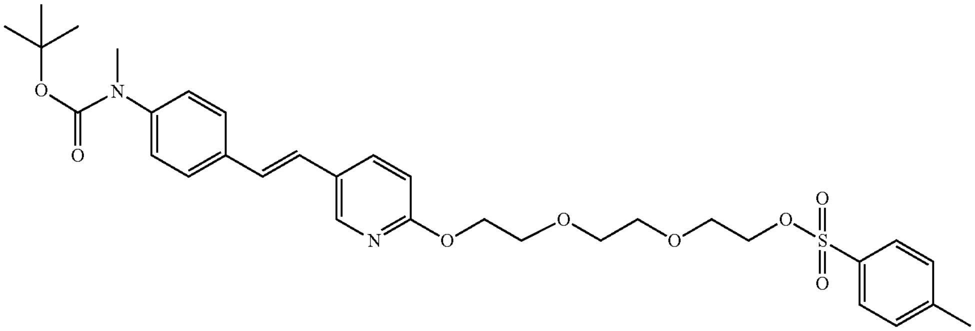 [SMILES: Cc1ccc(S(=O)(=O)OCCOCCOCCOc2ccc(/C=C/c3ccc(N(C)C(=O)OC(C)(C)C)cc3)cn2)cc1]

comprising the steps of:

(a) methylation of the Boc-protected Formula III in a suitable methylating agent to obtain the compound of Formula IV with the compound of Formula V being present at less than 10 ppm;

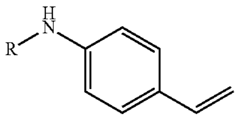

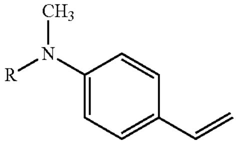

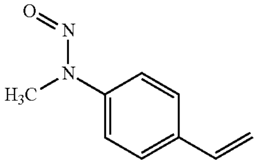

(R) is Boc (b) reacting the compounds of Formula IV and Formula VI in a suitable solvent in the absence of an organic base using about 2.0 to 3.0 mole equivalents of inorganic base, about 1.5 to 2.0 mole equivalents of phase transfer catalyst to obtain the compound of Formula VII wherein the compound of Formula VIII is present at less than 10 ppm; and Formula VI

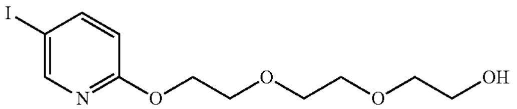

Formula VII

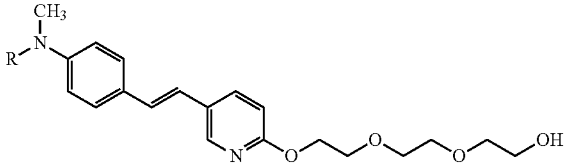

Formula VIII

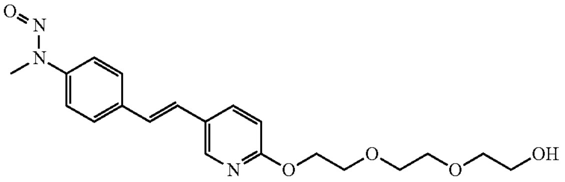

(c) introducing a tosylate leaving group into the compound of Formula VII to obtain a compound of Formula X free of the N-Nitroso compound of Formula XI.

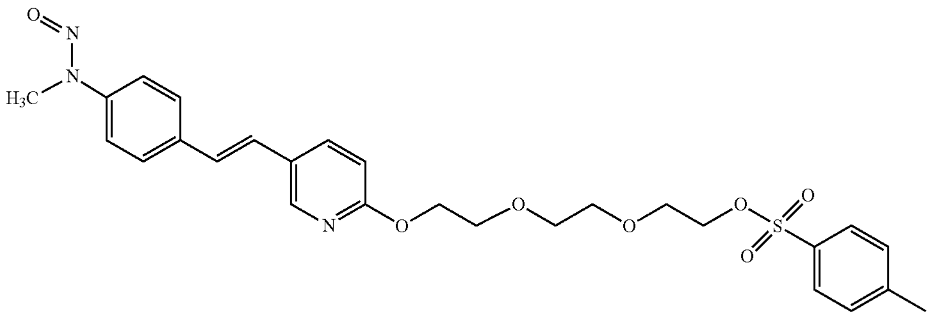

According to the present invention, the solvent used is selected from the group comprising of nitriles, alcohols, ketones, esters, halogenated hydrocarbons, ethers, amides, dialkylsulfoxides, sulfolane, water and mixtures thereof, which are further selected from the group comprising of acetonitrile, propionitrile, butyronitrile, valeronitrile, methanol, ethanol, n-propanol, isopropanol, n-butanol, acetone, methyl ethyl ketone, methyl isobutyl ketone, ethyl acetate, propyl acetate, isopropyl acetate, butyl acetate, dichloromethane (DCM), chloroform, dichloroethane, chlorobenzene, diethyl ether, methyl tert-butyl ether (MTBE), diisopropyl ether, tetrahydrofuran (THF), dimethylformamide, dioxane, dimethylsulfoxide, diethylsulfoxide, dibutylsulfoxide, pentane, hexane, heptane, octane, cyclohexane, cyclopentane, toluene and xylene, water and mixtures thereof.

According to the present invention, the N-protecting group is selected from group comprising of Boc, trityl, 4-methoxy trityl and the like.

According to the present invention, the leaving group is selected from group comprising of mesylate, nosylate, phenoxyphenyl sulfonate, triflate, halide and the like.

According to the present invention, the methylating agent is selected from the group comprising of methanol, dimethyl carbonate, formaldehyde/formic acid, carbon dioxide/hydrogen, methyl iodide, dimethylsulfate, peroxides, dimethylsulfoxide and the like.

According to the present invention, the phase transfer catalyst is selected from the group comprising of cyclodextrin, benzyltriethylammonium chloride (TEBA), tetrabutylammonium bromide (TBAB), tetrabutylammonium chloride, tetrabutylammonium hydrogen sulfate, trioctylmethylammonium chloride, dodecyltrimethylammonium chloride, tetradecyltrimethylammonium chloride and the like, preferably tetrabutylammonium bromide (TBAB). The phase transfer catalyst often contain amine functionalities and using them in excess amount increases the availability of amines that can react with nitrosating agents and result in formation of undesirable nitrosamine impurities. Thus, controlling the mole ratio ensures that only the necessary amount is present, reducing the risk of side reactions. The phase transfer catalyst is used in present invention is about 1.0 to 2.0, preferably 1.5 to 2.0 mole equivalents of reactant.

According to the present invention, the inorganic base is selected from the group comprising of alkali and alkaline earth metal carbonates, bicarbonates, hydroxides and the like, wherein the alkali and alkaline earth metal are selected from sodium, potassium, magnesium, calcium and the like. The inorganic base is used in about 1.0 to 3.0, preferably 2.0 to 3.0 mole equivalents of reactant, as precise stoichiometry ensured that the base is fully consumed, leaving no excess to participate in unwanted side reactions, altering pH to range that facilitates nitrosation, leading to formation of unwanted nitrosamine impurities.

According to the present invention, organic base is an organic compound that can act like a base.

According to the present invention, nitrite free inorganic bases after radiolabelling are used in de-protection of the Boc group step to prevent the formation of N-Nitroso Florbetapir.

According to the present invention, the genotoxic undesirable nitrosamine impurity is selected from N-nitroso Florbetapir (Formula II), N-Nitroso AV-105, ((E)-2-(2-(2-((5-(4-(methyl(nitroso)amino)styryl)pyridin-2-yl)oxy) ethoxy)ethoxy)ethyl 4-methylbenzene sulfonate] (Formula XI), (E)-N-(4-(2-(6-(2-(2-(2-hydroxyethoxy)ethoxy)ethoxy) pyridin-3-yl)vinyl)phenyl)-N-methylnitrous amide] (Formula VIII), and [N-methyl-N-(4-vinylphenyl)nitrous amide] (Formula V), N-Nitroso mesylate compound of Formula XIII and other nitrosamine impurities selected from Nitrosodimethylamine (NDMA), N-Nitrosodiethylamine (NDEA), N-Nitrosodiisopropylamine (NDIPA/DIPNA), N-Nitrosoethylisopropylamine (EIPNA), N-Nitrosomethylethylamine (NMEA), N-Nitrosodipropylamine (NPDA), N-Nitrosodibutylamine (NBDA), N-Nitrosomethyldodecylamine, and N-Nitroso-N-methyl-N-tetradecylamine.

Formula II

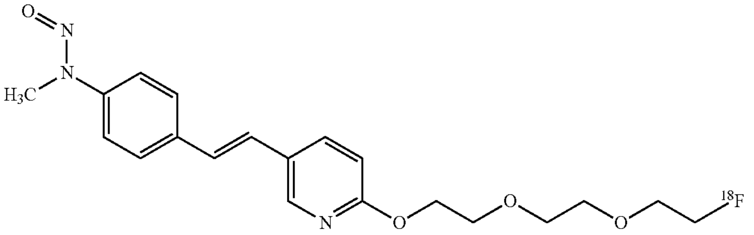

Formula XI

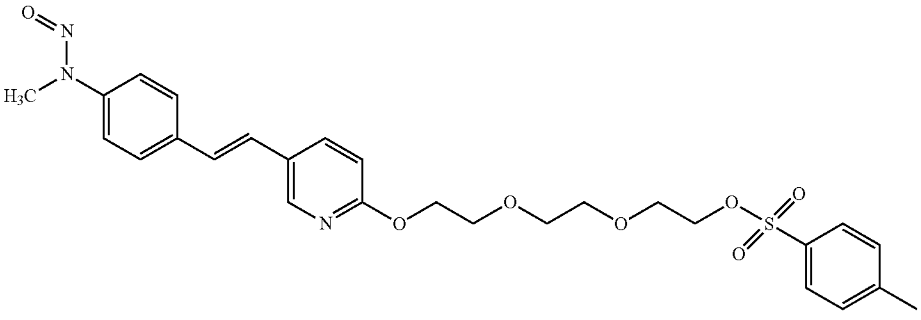

-continued

Formula VIII

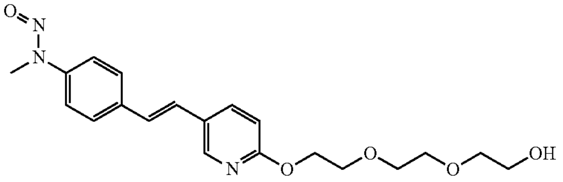

Formula X

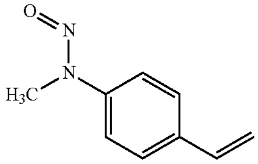

Formula XIII

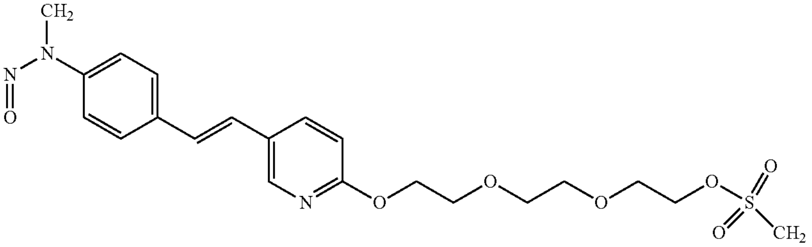

According to the present invention, the undesirable nitrosamine impurity in F18 Florbetapir is preferably N-nitroso Florbetapir of Formula II.

According to the present invention, the other impurities are chemical impurities selected from Florbetapir mesylate precursor of Formula XII, deboc Florbetapir mesylate precursor of Formula XIV, Impurity of Formula XV and chloro Florbetapir impurity of Formula XVI.

According to another embodiment, the present invention relates to the tosylate precursor of Florbetapir, AV-105, of Formula X that is free of undesirable polymorphic forms of the AV-105 tosylate precursor of Florbetapir.

According to the present invention, the undesirable polymorphs of AV-105 tosylate precursor of Formula X are selected from polymorphic Form A, Form B and both.

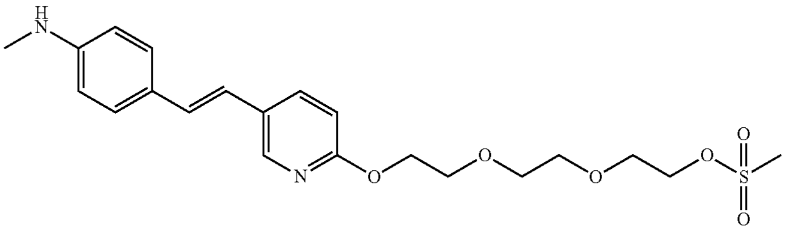

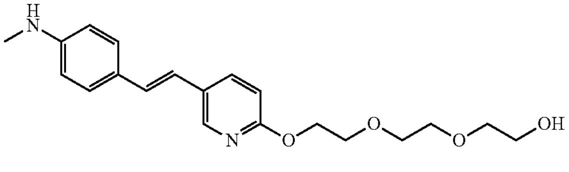

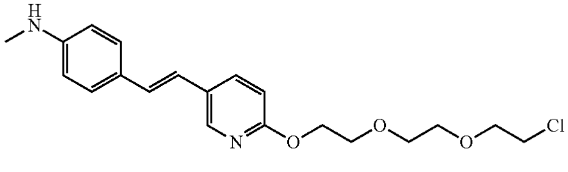

According to the present invention, the Florbetapir precursors are isolated using one or more work-up processes such as extraction, washing, filtration and the like. The Florbetapir precursors obtained are then optionally crystallized from suitable organic solvent to remove undesirable impurities. The suitable organic solvent for crystallization is selected from the group comprising of alcohols, esters, ketones, hydrocarbon, halogenated hydrocarbons, water or mixtures thereof; particularly methanol, ethanol, n-propanol, isopropanol, n-butanol, isobutanol, tert-butanol, methyl acetate, ethyl acetate, isopropyl acetate, tertiary butyl acetate, acetone, methyl ethyl ketone, hexane, heptane, toluene, xylene, dichloromethane, water or mixtures thereof.

The polymorphic Form A and Form B of the AV-105 tosylate precursor of Florbetapir are as disclosed in WO2024107620.

According to another embodiment, the present invention relates to solid polymorphic form of Formula IX free of undesirable nitrosamine impurities, wherein when:

(i) R=Boc and Lv=OMs (mesylate);

(ii) R=Boc and Lv=ONs (nosylate); or (iii) R=Boc and Lv=4-(benzyloxy)benzene-1-sulfonyl According to another embodiment, the present invention provides a solid polymorphic form of mesylate precursor of compound of Formula XII, when R=Boc and Lv=OMs (mesylate).

Formula XII

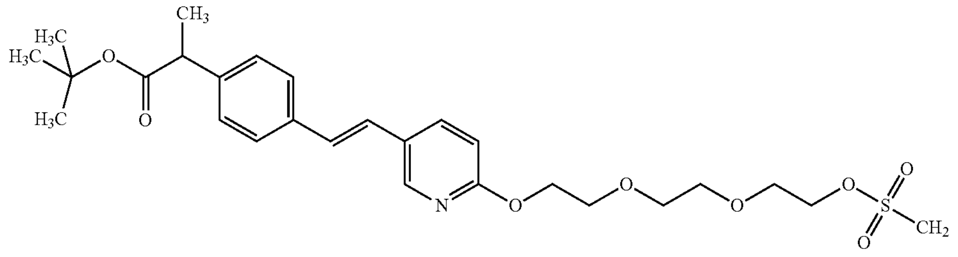

According to another embodiment, the present invention relates to the crystalline form of mesylate precursor of Formula XII, when R=Boc and Lv=OMs (mesylate), is characterised by X-ray powder diffraction pattern using CuKα radiation comprising a peak at diffraction angle 2θ of 17.4°, and one or more peaks selected from the group consisting of 10.9° and 13.0°, with a deviation of ±0.2°.

According to another embodiment, the crystalline form of mesylate precursor of Formula XII, when R=Boc and Lv=OMs (mesylate) is characterized by the X-ray powder diffraction pattern using CuKα radiation comprising peaks at diffraction angles 2θ of 17.4° and 10.9°.

According to another embodiment, the crystalline form of mesylate precursor of Formula XII, when R=Boc and Lv=OMs (mesylate) is characterized by an X-ray powder diffraction pattern using CuKa radiation comprising peaks at diffraction angles 2θ of 17.4° and 13.0°.

According to another embodiment, the crystalline form of mesylate precursor of Formula XII, when R=Boc and Lv=OMs (mesylate) is characterized by an X-ray powder diffraction pattern using CuKa radiation comprising peaks at diffraction angles 2θ of 17.4° and 21.8°.

In further embodiments, the crystalline form of mesylate precursor of Formula XII, when R=Boc and Lv=OMs (mesylate) is characterized by an X-ray powder diffraction pattern using CuKα radiation comprising a peak at diffraction angle 2θ of 17.4° and one or more peaks selected from the group consisting of 10.9°, 13.0° and 21.8, wherein the X-ray powder diffraction pattern using CuKα radiation further comprises a peak at diffraction angle 2θ of 2.2°; with deviation of ±0.2°.

The present embodiments also provide the mesylate precursor of Formula XII, when R=Boc and Lv=OMs (mesylate) which is crystalline and is characterized by an X-ray powder diffraction pattern using CuKα radiation comprising two peaks at diffraction angles 2θ, wherein the two peaks are selected from the group consisting of 2.2, 6.5, 10.9°, 13.0°, 17.4 21.8 and 26.3; with deviation of ±0.2°.

In further embodiments, the crystalline form mesylate precursor of Formula XII, when R=Boc and Lv=OMs (mesylate) is characterized by an X-ray powder diffraction pattern using CuKα radiation comprising peaks depicted in FIG. 1.

According to another embodiment, the present invention relates to the crystalline form of mesylate precursor of Formula XII, when R=Boc and Lv=OMs (mesylate), is characterised by Fourier Transform Infra Red (FTIR) absorptions peaks at 2974, 1708, 1340, 1285, 1251, 1153, 1106, 1046, 973, 948 and 908 $cm^{-1}$.

Figure 2:
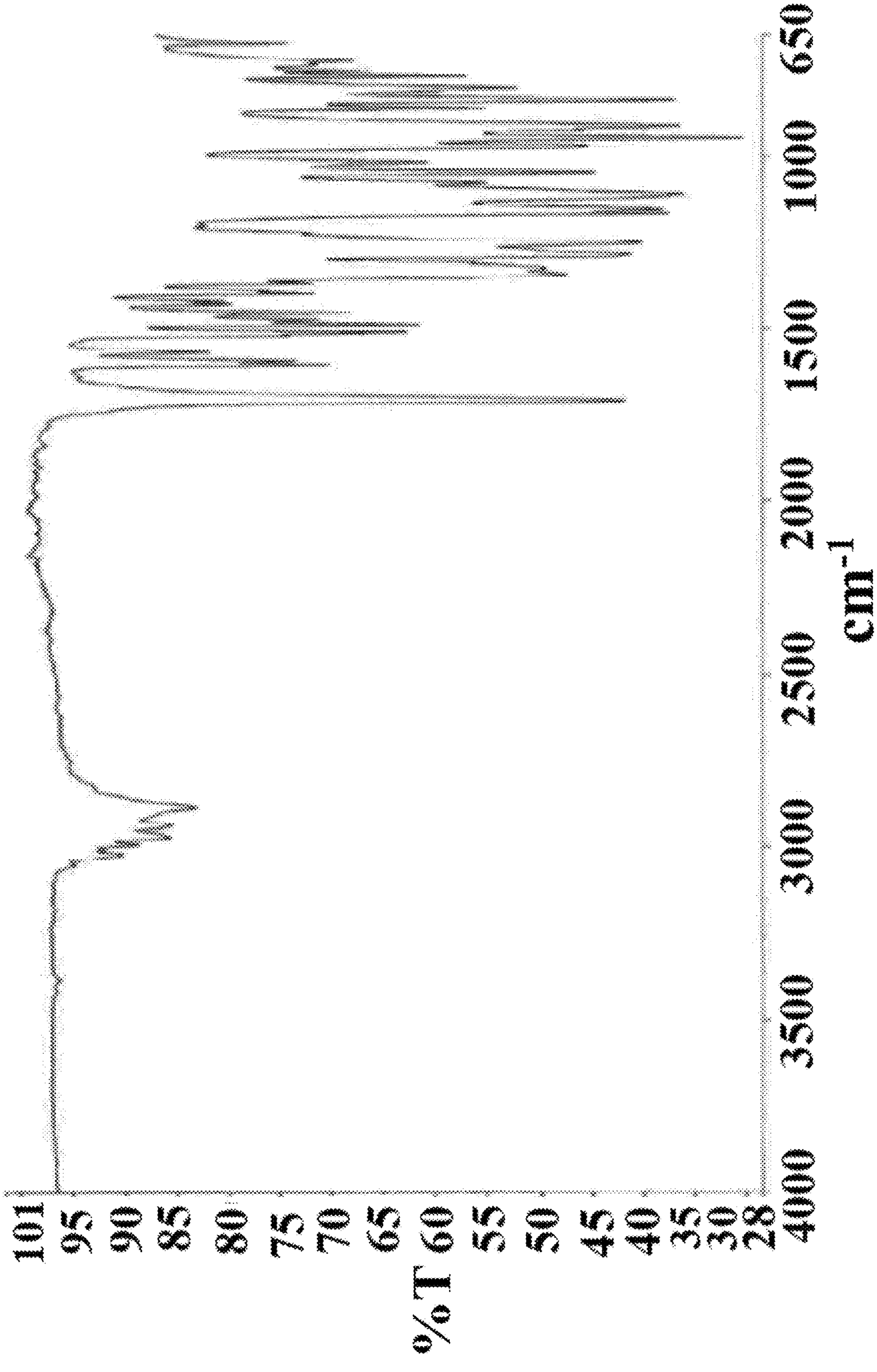
FIG. 2: shows the infrared spectrum crystalline form mesylate precursor of Formula XII.

In further embodiments, the crystalline form mesylate precursor of Formula XII, when R=Boc and Lv=OMs (mesylate) is characterized by Fourier Transform Infra Red (FTIR) spectrum depicted in FIG. 2.

According to another embodiment, the present invention relates to the crystalline form of mesylate precursor of Formula XII, when R=Boc and Lv=OMs (mesylate), is characterised by a melting point of 62° C.+/−0.15° C., determined by known melting point determination methods like determined by differential enthalpic analysis (DSC) and melting point determination apparatus.

This invention encompasses the crystalline form mesylate precursor of Formula XII, when R=Boc and Lv=OMs (mesylate) that is more thermodynamically stable and provide better and/or more reliable properties than prior art.

A solid stable form of precursor has proven to be important in helping local PET imaging centers perform a smooth and consistent conversion of precursors into florbetapir F-18, making it suitable for human use, with highly reduced scope of contamination and very easy to handle in already sensitive handling environment of eluting and infusing time sensitive radioisotopes, preferably F18 as per present invention.

According to another embodiment, the crystalline form mesylate precursor of Formula XII, when R=Boc and Lv=OMs (mesylate) characterized by any of above is prepared comprising the steps of:

(i) dissolving mesylate precursor of Formula XII, when R=Boc and Lv=OMs (mesylate) in solvent;

(ii) crystallizing the crystalline form mesylate precursor of Formula XII, when R=Boc and Lv=OMs (mesylate).

According to the present invention, wherein the solvent used for preparation of crystalline mesylate precursor of Formula XIII is selected from methanol, ethanol, propanol and the like.

According to present invention, the process step involving dissolving comprises of heating, and stirring to obtain a clear solution. The crystallization step involves cooling, filtration, washing the crystalline product with suitable solvent and drying with or without vacuum.

According to present invention, the crystalline form mesylate precursor of Formula XII, when R=Boc and Lv=OMs (mesylate) is prepared without using any cumbersome chromatographic separation and only involves crystallization, that makes the process handling simple, easier, reduces cycle time and further the crystalline mesylate precursor is stable and easy to handle. These attributes makes the process robust and consistently provides crystalline form mesylate precursor of Formula XII in higher yield and purity.

According to another embodiment, the crystalline form mesylate precursor of Formula XII, when R=Boc and Lv=OMs (mesylate) characterized by any of above is prepared, comprising the steps of:

(a) methylation of the Boc-protected Formula III in a suitable methylating agent to obtain the compound of Formula IV with the compound of Formula V being present at less than 10 ppm;

Formula III

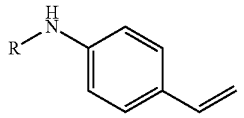

Formula IV

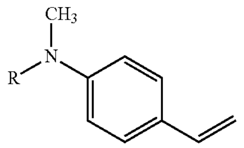

Formula V

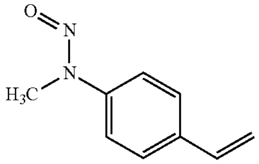

(R) is Boc;

(b) reacting the compounds of Formula IV and Formula VI in a suitable solvent in the absence of an organic base using about 2.0 to 3.0 mole equivalents of inorganic base, about 1.5 to 2.0 mole equivalents of phase transfer catalyst to obtain the compound of Formula VII wherein the compound of Formula VIII is present at less than 10 ppm; and

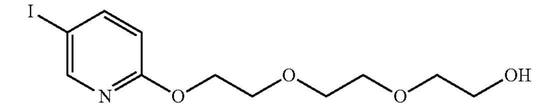

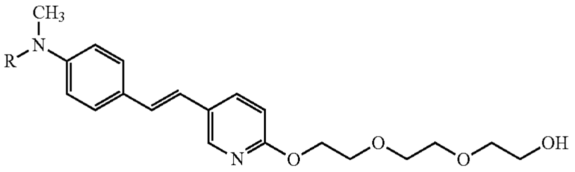

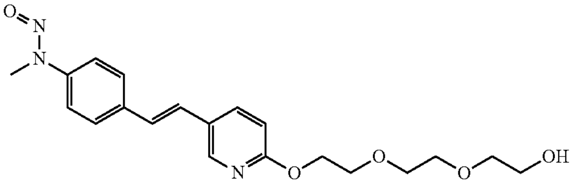

(R) is Boc;

(c) introducing a mesylate leaving group into the compound of Formula VII in a suitable solvent to obtain a crystalline mesylate precursor compound Formula XII free of the N-Nitroso compound of Formula XIII.

Formula XII

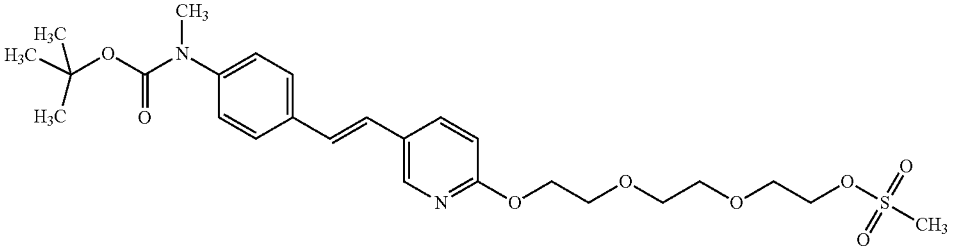

Formula XIII

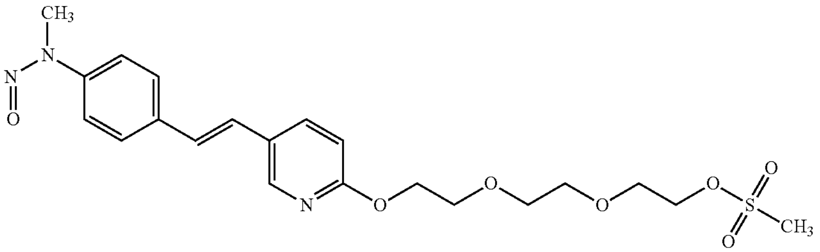

According to another embodiment, the crystalline form mesylate precursor of Formula XII, when R=Boc and Lv=OMs (mesylate) characterized by any of above is used as a precursor for the preparation of F18 Florbetapir.

According to another embodiment, the crystalline form mesylate precursor of Formula XII, when R=Boc and Lv=OMs (mesylate) is further used for the preparation of F18 Florbetapir, comprising the steps of:

(a) methylation of the Boc-protected Formula III in a suitable methylating agent to obtain the compound of Formula IV with the compound of Formula V being present at less than 10 ppm;

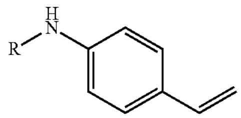

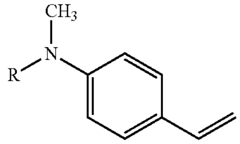

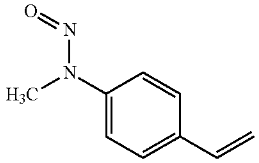

(R) is Boc;

(b) reacting the compounds of Formula IV and Formula VI in a suitable solvent in the absence of an organic base using about 2.0 to 3.0 mole equivalents of inorganic base, about 1.5 to 2.0 mole equivalents of phase transfer catalyst to obtain the compound of Formula VII wherein the compound of Formula VIII is present at less than 10 ppm;

Formula VI

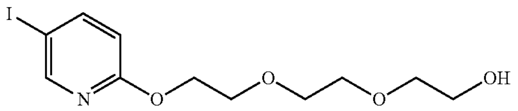

Formula VII

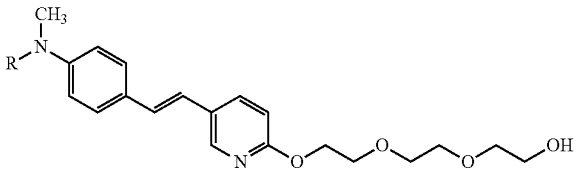

Formula VIII

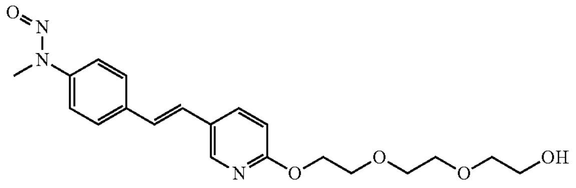

(R) is Boc;

(c) introducing a mesylate leaving group into the compound of Formula VII in a suitable solvent to obtain a crystalline mesylate precursor compound Formula XII free of the N-Nitroso compound of Formula XIII; and (d) radiolabelling a compound of Formula XIV with a F-18 fluorinating agent and removing the N-protecting agent to obtain a compound of Formula I wherein the F18 Florbetapir obtained has nitrosamine impurities less than 100 ppm, preferably less than 50 ppm and more preferably less than 20 ppm and other impurities less than 10 μg/ml, preferably less than 5 μg/ml, more preferably less than 3 μg/ml.

The present invention relates to a radiopharmaceutical composition comprising of:

(i) F18 Florbetapir; and (ii) pharmaceutically acceptable excipients, wherein the radiopharmaceutical composition has undesirable nitrosamine impurities less than 100 ppm, preferably less than 50 ppm and more preferably less than 20 ppm and other impurities less than 10 μg/ml, preferably less than 5 μg/ml, more preferably less than 3 μg/ml;

and wherein the radiopharmaceutical composition has a radiochemical purity of at least 90% after 10 hours of storage at a temperature of about 2-30° C.

The present invention relates to radiopharmaceutical composition comprising:

(i) F18 Florbetapir; and (ii) pharmaceutically acceptable excipients wherein F18 Florbetapir is prepared in a process comprising the steps of:

(a) methylation of the compound of Formula III in a suitable methylating agent to obtain the compound of Formula IV and with Formula V being present at less than 10 ppm;

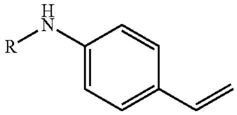

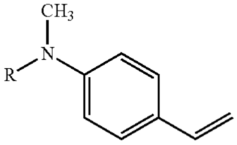

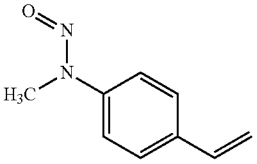

(R) is N-protecting group (b) reacting the compounds of Formula IV and Formula VI in a suitable solvent in the absence of an organic base using about 2.0 to 3.0 mole equivalents of inorganic base, about 1.5 to 2.0 mole equivalents of phase transfer catalyst to obtain the compound of Formula VII wherein the compound of Formula VIII is present at less than 10 ppm;

Formula VI

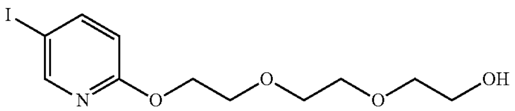

-continued

Formula VII

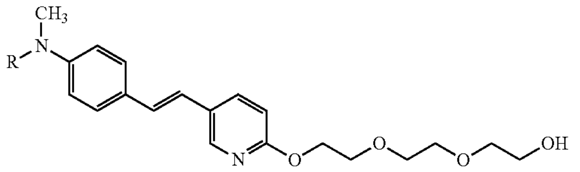

Formula VIII

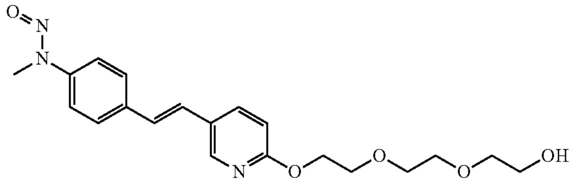

(c) introducing a leaving group into the compound of Formula VII to obtain a compound of Formula IX free of N-Nitroso derivative of Formula IX;

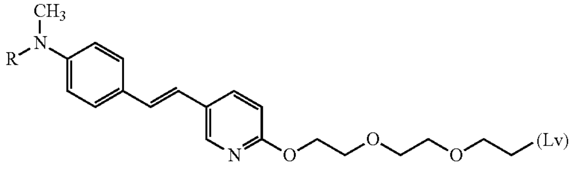

wherein (R) is a N-protecting group and [Lv] is leaving group; and (d) radiolabeling a compound of Formula IX with a F-18 fluorinating agent and removing the N-protecting group, to obtain a compound of Formula I wherein the F18 Florbetapir obtained has undesirable nitrosamine impurities less than 100 ppm, preferably less than 50 ppm and more preferably less than 20 ppm and other impurities less than 10 μg/ml, preferably less than 5 μg/ml, more preferably less than 3 μg/ml;

and wherein the radiopharmaceutical composition has a radiochemical purity of at least 90% after 10 hours of storage at a temperature of about 2-30° C.

According to present invention, the radiopharmaceutical composition, preferably have radiochemical purity of at least 98% after 10 hours of storage at a temperature of about 2-30° C.

According to the present invention, the solvents, reagents, buffers, excipients, purification cartridges are free from any nitrite source.

According to the present invention, the pharmaceutically acceptable excipients of the radiopharmaceutical composition further comprises one or more of radioprotectants, radical scavengers, stabilizers, co-solvent and the like, such as those selected from sodium ascorbate, ascorbic acid, gentisic acid, glutamate, monothioglycerol, propyl gallate, niacinamide, p-amino benzoic acid, hydroxy benzoic acid, cysteine, alcohol and combinations thereof, preferably sodium ascorbate and alcohol.

According to another embodiment, the present invention provides a radiopharmaceutical composition of F18 Florbetapir, prepared using the crystalline mesylate precursor of Formula XII.

According to the present invention, the radiopharmaceutical composition of F18 Florbetapir free of undesirable genotoxic nitrosamine impurities contains 500MBq to 1900 MBq of florbetapir F 18 at the end of synthesis.

According to the present invention, the radiolablleing to obtain F18 Florbetapir can be performed using F18 radiolabelling cassette by Trais AllinOne 36 synthesis Module or other known F18 radiolabelling modules available in prior art.

According to another embodiment, the present invention relates to a process for preparing Florbetapir of Formula I essentially free of undesirable nitrosamine impurities, wherein the process comprises of drying the compound of precursors of Fluorine-18 Florbetapir in controlled humidity drying conditions.

According to the present invention, the controlled humidity drying condition is comprised of drying conditions with relative humidity of up to about 90%.

According to the present invention, the F18 Florbetapir precursors are subjected to drying to remove solvent under controlled humidity conditions, wherein the relative humidity during drying is up to about 90%. The drying method used is selected from the group comprising of vacuum drying, fluidized bed drying, freeze drying, rotary vacuum drying convection drying and the like as known in the literature. The relative humidity is controlled by using a method selected from the group comprising of use of de-humidifier, desiccant dryer method and the like. The drying is carried out at a temperature from about room temperature to 200° C., for 1-50 h. The temperature of the dryer is increased optionally in stepwise manner, starting from lower temperature range to higher range, by keeping each range of temperature constant for about 1-20 h.

According to another embodiment of the present invention, the source of nitrite/nitrate and any source of secondary amine is tested and appropriately controlled in raw material/reagents/solvents and upstream process during the preparation of Florbetapir.

The present invention includes the use of any of the radiopharmaceutical compositions and compounds prepared herein as a medicament for the treatment or diagnosis of a disease or condition selected from AD or other disease associated with build-up of amyloid-β (Aβ) aggregates and for selecting patients who are indicated for amyloid beta-directed therapy.

The term F18 means fluorine isotope $^{18}F$.

The radiochemical purity analysis of radiolabelled composition is carried out using ascending paper chromatography.

EXAMPLES

General:

An automated radiosynthesizer Synthra® RNPlus Research (Hamburg, Germany), containing 2 reactors, HPLC semi preparative C18 column, UV (λ=254 nm) and gamma-ray detectors was used for Florbetapir radiosynthesis, purification and reformulation. Sep-Pak™ Accel™ Plus Light QMA cartridges (Water, Ireland) were preconditioned with 5 mL of Sodium Bicarbonate Injection USP (8.4%) followed by 10 mL of Milli-Q® water. Sep-Pak™ Plus Short C18 cartridges (Waters, Ireland) were preconditioned with 5 mL ethanol followed by 10 mL of Milli-Q® water. Sterile syringe filters (Vented Millex®-GV, 0.22 μm) were used for reformulation. Analytical HPLC was carried out on a Waters system equipped with a binary HPLC pump 1525, UV/visible detector 2489 and NaI (Tl) scintillation detector connected to a Waters e-SAT/IN interface module using a ZORBAX Eclipse XDB-C18 column (4.6×150 mm, 5 μm, Agilent Technologies). The chromatograms were acquired and analyzed with the Breeze™ 2 software (Waters).

Example 1: Chemical synthesis of Florbetapir precursors: (E)-2-[2-[2-[5-[4-[tert-butoxycarbonyl [methyl]amino] styryl]pyridine-2-yloxy]ethoxy] ethoxy]ethyl-4-methylbenzene sulfonate (AV-105) and (E)-2-(2-(2-((5-(4-((tert-butoxycarbonyl) (methyl)amino)styryl)pyridin-2-yl)oxy)ethoxy) ethoxy)ethyl methanesulfonate (mesylate precursor)

Step a:

The Boc protected compound of formula III (100 g) dissolved in dimethylformamide (250 ml) was slowly added to a solution of sodium hydride (27.36 g) in dimethylformamide (300 ml) at a temperature between 0 to 10° C. The resulting reaction mass was stirred at room temperature for about 20-25 minutes. A solution of methyl iodide (130 g) in dimethylformamide (150 ml) was then slowly added to the reaction mixture and stirred the reaction mixture for about 6 to 24 hours. Upon completion of reaction, the reaction mixture was diluted with ice-cold water and extracted with ethyl acetate. The solvent was vaporized to obtain (tert-Butyl methyl(4-vinylaniline) carbamate) compound of formula IV.

Nitrosamine Impurity: N-Nitroso Compound of Formula V: Less than 10 ppm

Step b:

The (tert-Butyl methyl(4-vinylaniline) carbamate) compound of formula IV (66.04 g), (2-(2-(2-(5-iodopyridin-2-yloxy)ethoxy)ethoxy) ethanol) (100 g), tert-butyl ammonium bromide (149.7 g) and potassium carbonate (97 g) were taken in dimethylformamide (750 ml). To the reaction mixture, added palladium acetate (1.9 g), heated to a temperature of 65° C. and stirred for about 6 to 24 hours. The reaction was monitored for completion. Upon completion of reaction, ethyl acetate and celite were added and the layers were separated after stirring. The solvent from organic layer was evaporated and the oily mass obtained was treated with methyl tert-butyl ether (MTBE) at 45° C. The reaction mixture was then subjected to evaporation at low temperature and the resulting mixture was treated with MTBE and cyclohexane to obtain solid (E)-tert-butyl N-(4-(2-(6-(2-(2-(2-hydroxyethoxy) ethoxy)ethoxy)pyridin-3-yl)vinyl)phenyl)-N-methylcarbamate of formula VII.

Nitrosamine Impurity: N-Nitroso Compound of Formula VIII: Less than 10 ppm

Step c:

Preparation of (E)-2-[2-[2-[5-[4-[tert-butoxycarbonyl [methyl]amino] styryl] pyridine-2-yloxy]ethoxy]ethoxy] ethyl-4-methylbenzene sulfonate (AV-105): To (E)-tert-butyl N-(4-(2-(6-(2-(2-(2-hydroxyethoxy)ethoxy)ethoxy) pyridin-3-yl)vinyl)phenyl)-N-methylcarbamate of formula VII (15 g) in dichloromethane (300 ml), added triethyamine (8.28 g), potassium carbonate (11 g) and dimethylamino pyridine (0.3 g). The reaction mixture was stirred at room temperature for about 25 minutes, the cooled to about 10° C. and a solution of para-Toluenesulfonyl chloride (14 g) in dichloromethane (100 ml) was slowly added. The reaction mixture was then stirred at room temperature for about 18-24 hours and the progress of reaction was monitored by HPLC. Upon completion of reaction, the reaction was treated with aq. potassium carbonate. The solvent from organic layer was evaporated, the oily mass was first purified using chromatography with ethylacetate/heptane, the purified oil (E)-2-[2-[2-[5-[4-[tert-butoxycarbonyl [methyl] amino] styryl]pyridine-2-yloxy]ethoxy] ethoxy]ethyl-4-methylbenzene sulfonate (AV-105), was then taken in acetonitrile (2500 ml) for radiolabelling reaction.

HPLC purity NLT 95%; N-Nitroso AV-105 Less than 10 ppm

Step d: Preparation of (E)-2-(2-(2-((5-(4-((tert-butoxycarbonyl)(methyl)amino)styryl) pyridin-2-yl) oxy)ethoxy)ethoxy)ethyl methanesulfonate (mesylate precursor)

To (E)-tert-butyl N-(4-(2-(6-(2-(2-(2-hydroxyethoxy) ethoxy)ethoxy)pyridin-3-yl)vinyl)phenyl)-N-methylcarbamate of formula VII (15 g) in dichloromethane (300 ml), added triethyamine (8.28 g), potassium carbonate (11 g) and dimethylamino pyridine (0.3 g). The reaction mixture was stirred at room temperature for about 25 minutes, the cooled to about 10° C. and a solution of methanesulfonyl chloride (8.24 g) in dichloromethane (100 ml) was slowly added. The reaction mixture was then stirred at room temperature for about 24 hours and the progress of reaction was monitored by HPLC. Upon completion of reaction, added water (500 ml) and separated the layers. The solvent from organic layer was evaporated, and treated with ethyl acetate/heptane at 35-40° C. to obtain a solid that was crystallized from ethanol and dried under vacuum to obtain white solid crystalline (E)-2-(2-(2-((5-(4-((tert-butoxycarbonyl)(methyl)amino) styryl)pyridin-2-yl)oxy)ethoxy) ethoxy)ethyl methanesulfonate having melting point of 62° C., characteristic X-ray diffraction pattern (XRPD) of FIG. 1 and FTIR of FIG. 2.

HPLC purity: 99.7%; N-Nitroso mesylate precursor of Formula XIII Less than 10 ppm XRPD data for crystalline (E)-2-(2-(2-((5-(4-((tert-butoxycarbonyl)(methyl)amino)styryl)pyridin-2-yl)oxy) ethoxy)ethoxy)ethyl methanesulfonate:

XRPD patterns were collected using diffractometers using an incident beam of Cu radiation produced using an Optix long, fine-focus source. An elliptically graded multilayer mirror was used to focus CuKα X-rays through the specimen and onto the detector. A beam-stop, short antiscatter extension, and an antiscatter knife edge were used to minimize the background generated by air. Soller slits for the incident and diffracted beams were used to minimize broadening from axial divergence. Diffraction patterns were collected using a scanning position-sensitive detector located 240 mm from the specimen and Data Collector software.

TABLE 1

Observed peaks for crystalline (E)-2-(2-(2-((5-(4-((tert-butoxycarbonyl)(methyl)amino)styryl) pyridin-2-yl)oxy)ethoxy)ethoxy)ethyl) methanesulfonate for XRPD with CuKα radiation.

| °2θ | Relative Intensity |
|---|---|
| 2.2 | 34.4 |
| 2.5 | 3.32 |
| 4.4 | 2.06 |
| 6.5 | 29.06 |
| 7.4 | 2.96 |
| 10.9 | 35.66 |
| 13.0 | 56.8 |
| 15.3 | 3.85 |
| 17.4 | 100 |
| 18.7 | 2.37 |
| 20.0 | 5.39 |
| 21.8 | 37.77 |
| 23.1 | 1.75 |

TABLE 1-continued

| Observed peaks for crystalline (E)-2-(2-(2-((5-(4-((tert-butoxycarbonyl)(methyl)amino)styryl) pyridin-2-yl)oxy)ethoxy)ethoxy)ethyl) methanesulfonate for XRPD with CuKα radiation. | |
|---|---|
| °2θ | Relative Intensity |
| 26.3 | 6.85 |
| 28.5 | 4.38 |
| 32.4 | 1.0 |
| 39.8 | 0.84 |

FTIR data for crystalline (E)-2-(2-(2-((5-(4-((tert-butoxycarbonyl)(methyl)amino)styryl)pyridin-2-yl)oxy)ethoxy)ethoxy)ethyl methanesulfonate:

FTIR spectrum were collected using Perkin Elmer Spectrum ES Version 10.5.2. The absorption peaks were observed at 2974, 1708, 1340, 1285, 1251, 1153, 1106, 1046, 973, 948, 908 $cm^{-1}$.

Example 2

Preparation of F18 Florbetapir: Radiolabelling and Deprotection: [18F] Fluoride produced via the $^{18}O(p,n)^{18}F$ nuclear reaction using the IBA Cyclone® 18/9 cyclotron was delivered to the Synthra® RNplus Research automated synthesis module. The [18F] Fluoride was trapped on a preconditioned Sep-Pak® QMA Plus Light cartridge and was then eluted with about 2 ml mixture of $K_2CO_3$ (2.7 mg) and Kryptofix®2.2.2 (15 mg) in a 5/1 (v/v) solution of acetonitrile/water into the reactor. The [K/Kryptofix]+ 18F-complex was dried at 110° C. for about 10 min under helium flow and/or vacuum in a reactor. (E)-2-[2-[2-[5-[4-[tert-butoxycarbonyl [methyl]amino] styryl]pyridine-2-yloxy] ethoxy] ethoxy]ethyl-4-methylbenzene sulfonate (AV-105) (4 mg) or (E)-2-(2-(2-((5-(4-((tert-butoxycarbonyl)(methyl)amino)styryl)pyridin-2-yl)oxy)ethoxy) ethoxy)ethyl methanesulfonate (4 mg) in acetonitrile (1 ml) was added to the reactor and heated to about 110° C. for about 10-15 minutes. A solution of about 1 ml hydrochloric acid was added and stirred for another 10 minutes and the reaction mixture was neutralized using sodium hydroxide solution upon cooling to obtain a crude reaction mixture.

Example 3

Semi-preparative HPLC purification method: The crude reaction mixture was loaded onto the first Sep-Pak C18 Plus cartridge. The crude F18 Florbetapir was eluted with 3 mL of acetonitrile and was further diluted with about 2 mL of ammonium acetate solution (20 mM) containing 5% of sodium ascorbate. The solution was then injected to a semi-preparative column and eluted using solution of acetonitrile/ammonium acetate and the best fraction was loaded on Sep-Pak C18 Plus cartridge. F18 Florbetapir was then eluted with 3 mL of USP ethanol.

The final drug product F18 Florbetapir was dispensed into a sterile vacuum vial by passing through a sterile filter attached to the sterile vial containing a solution of 0.7% (w/v) sodium ascorbate dissolved in 20 ml of sterile 0.9% sodium chloride. The eluate was diluted to 30 mL sterile 0.9% sodium chloride.

Example 4: Quality Control

An aliquot was removed for quality control tests. Analytical HPLC was performed to determine the chemical and radiochemical purity.

The tests for quality control either for final product or precursors included tests for product appearance, chemical identity, radiochemical purity, chemical purity, residual solvent and a bacterial endotoxins test was also completed and presented in Table 2.

The product appearance test was completed by visual inspection and the test was passed if the solution was colourless, clear and free of particulates. Chemical identity of the radioactive product as F18 Florbetapir was determined by analytical HPLC co-elution of the non-radioactive standard. Analytical HPLC of the product was performed to determine the radiochemical and chemical purity. The residual solvent test was completed by gas chromatography to measure the presence of ethanol and acetonitrile. The bacterial endotoxins test was completed using an Endosafe nexgen-PTS testing spectrophotometer and the test was passed if there were less than 175 EU in the total product volume.

TABLE 2

| Test results of F18 Florbetapir of present invention at 0 minutes and at 10 hours: | | | |
|---|---|---|---|
| Test | Specifications | Result at 0 minutes | Result at 10 hours |
| Chemical purity | Florbetapir (NLT 98%)<br>Total impurities (NMT 2%) | Conforms | Conforms |
| Radiochemical purity | F18-Florbetapir (NLT 98%) | 99% | 99% |
| 19F Florbetapir | NMT 5 ug/mL @ Expiry | Conforms | Conforms |
| Residual solvent | Heptane (NMT 5000 ppm) | Not detected | Not detected |
| | Acetonitrile (NMT 410 ppm) | 4 ppm | 4 ppm |
| | Dichloromethane (NMT 600 ppm) | Not detected | Not detected |
| | Tert-Butanol (NMT 3500 ppm) | Not detected | Not detected |
| | DMF (NMT 880 ppm) | Not detected | Not detected |
| | MTBE (NMT 5000 ppm) | Not detected | Not detected |
| | Ethyl acetate (NMT 5000 ppm) | Not detected | Not detected |
| Nitrosamine impurities | | | |
| NDMA | NMT 1920 ppm | Less than 50 ppm | Less than 50 ppm |
| NDEA | NMT 530 ppm | Less than 50 ppm | Less than 50 ppm |
| N-Nitroso Formula VIII | NMT 2000 ppm | Less than 50 ppm | Less than 50 ppm |
| N-Nitroso Formula V | NMT 2000 ppm | Less than 50 ppm | Less than 50 ppm |
| N-Nitroso AV-105 | NMT 2000 ppm | Less than 50 ppm | Less than 50 ppm |
| N-Nitroso mesylate precursor Formula XIII | NMT 2000 ppm | Less than 50 ppm | Less than 50 ppm |

TABLE 2-continued

| Test results of F18 Florbetapir of present invention at 0 minutes and at 10 hours: | | | |
|---|---|---|---|
| Test | Specifications | Result at 0 minutes | Result at 10 hours |
| N-Nitroso Florbetapir | NMT 2000 ppm | Less than 50 ppm | Less than 50 ppm |
| Bacterial Endotoxins | NMT 12.5 EU/mL | Conforms | Conforms |

NMT: Not More than; NLT: Not Less Than; LOD: Limit of Detection: 1 ppm

What is claimed:

1. A crystalline compound of formula:

(Formula XII)

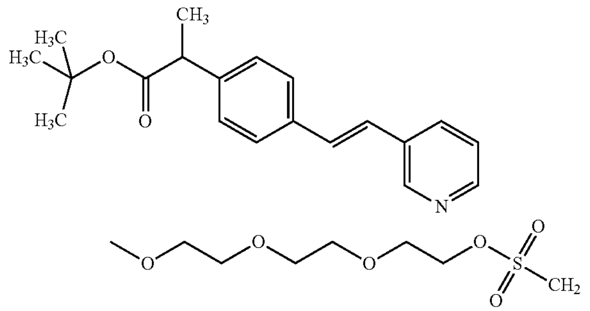

characterised by X-ray powder diffraction pattern comprising peaks at 17.4°, 10.9° and 13.0° 2θ±0.2°.

2. The compound according to claim 1, further comprising a X-ray powder diffraction pattern peak at 2.2° 2θ±0.2°.

3. The compound according to claim 1, further comprising a X-ray powder diffraction pattern peak at 6.5° 2θ±0.2°.

4. The compound according to claim 1, further comprising a X-ray powder diffraction pattern peak at 21.8° 2θ±0.2°.

5. The compound according to claim 1, characterized by the X-ray powder diffraction pattern comprising a peak 17.4° 2θ±0.2° and one or more peaks selected from the group consisting of 2.2, 6.5, 10.9°, 13.0° and 21.8≅0.2°.

6. The compound according to claim 1, characterized by the X-ray powder diffraction pattern comprising peaks at 2.2, 6.5, 10.9°, 13.0° 17.4°, 21.8 and 26.3 2θ±0.2°.

7. A crystalline compound of formula:

(Formula XII)

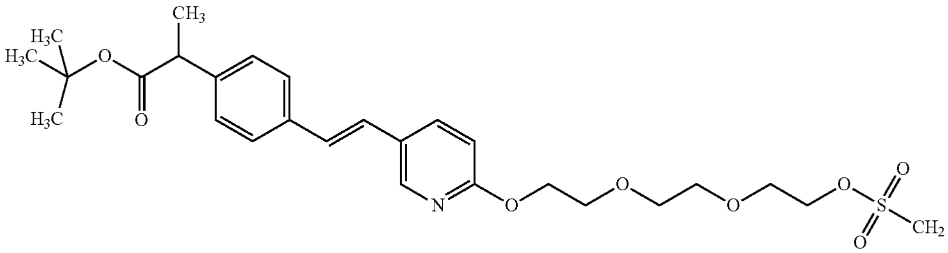

- characterised by infrared spectrum which exhibits characteristic absorptions expressed in $cm^{-1}$ at 2974, 1708, 1340, 1285 and 1251.

8. The compound according to claim 7, wherein the infrared spectrum further exhibits characteristic absorptions expressed in $cm^{-1}$ at 1153, 1106, 1046, 973, 948 and 908.

9. A crystalline compound of formula:

(Formula XII)

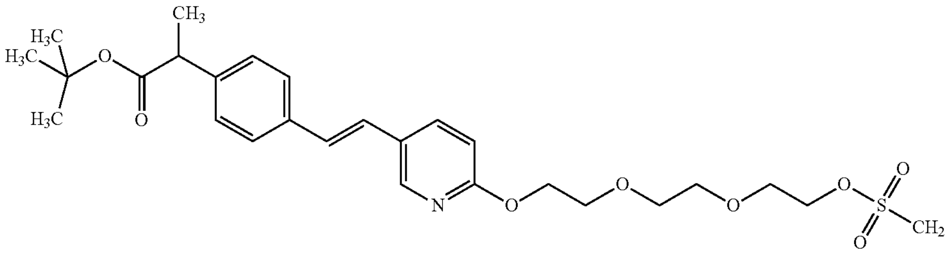

characterised by X-ray powder diffraction pattern comprising peaks at 2.2, 6.5, 10.9°, 13.0° 17.4° and 21.8±0.2° and an infrared spectrum with absorptions expressed in $cm^{-1}$ at 2974, 1708, 1340, 1285, 1251, 1153, 1106, 1046, 973, 948 and 908.

10. A process of preparing a compound of claim 1 comprising the steps of:

(i) dissolving mesylate precursor of Formula XII, when R=Boc and Lv=OMs (mesylate) in solvent; and (ii) crystallizing the crystalline form mesylate precursor of Formula XII, when R=Boc and Lv=OMs (mesylate).

11. The process according to claim 10, wherein the solvent is selected from methanol, ethanol and propanol.

12. The compound according to claim 1 for use as a precursor for preparation of F18 Florbetapir.

13. A process of preparing a compound of claim 7 comprising the steps of:

(i) dissolving mesylate precursor of Formula XII, when R=Boc and Lv=OMs (mesylate) in solvent; and (ii) crystallizing the crystalline form mesylate precursor of Formula XII, when R=Boc and Lv=OMs (mesylate).

14. The process according to claim 13, wherein the solvent is selected from methanol, ethanol and propanol.

15. The compound according to claim 7 for use as a precursor for preparation of F18 Florbetapir.

16. A process of preparing a compound of claim 9 comprising the steps of:

(i) dissolving mesylate precursor of Formula XII, when R=Boc and Lv=OMs (mesylate) in solvent; and (ii) crystallizing the crystalline form mesylate precursor of Formula XII, when R=Boc and Lv=OMs (mesylate).

17. The process according to claim 16, wherein the solvent is selected from methanol, ethanol and propanol.

18. The compound according to claim 9 for use as a precursor for preparation of F18 Florbetapir.

19. The compound according to claim 1, further characterised by an infrared spectrum which exhibits characteristic absorptions expressed in $cm^{-1}$ at 2974, 1708, 1340, 1285 and 1251.

20. The compound according to claim 7, further characterized by the X-ray powder diffraction pattern comprising peaks at 2.2, 6.5, 10.9°, 13.0° 17.4°, 21.8 and 26.3 2θ=0.2°.

* * * * *